United States Patent
Abdel-Magid et al.

(10) Patent No.: US 6,576,786 B2
(45) Date of Patent: Jun. 10, 2003

(54) PROCESS FOR PREPARING SUBSTITUTED CYCLOPENTANE DERIVATIVES AND NOVEL CRYSTALLINE STRUCTURES THEREOF

(75) Inventors: Ahmed F. Abdel-Magid, Ambler, PA (US); Hans-Ulrich Bichsel, Horhausen (CH); Daniel J. Korey, Yardley, PA (US); Gunther G. Laufer, Freiburg (DE); Erja A. Lehto, Zurich (CH); Sebastiano Mattei, Locarno (CH); Max Rey, Wallisellen (CH); Thomas W. Schultz, Richboro, PA (US); Cynthia Maryanoff, New Hope, PA (US)

(73) Assignee: Biocryst Pharmaceuticals Inc., Birmingham, AL (US)

( * ) Notice: Subject to any disclaimer, the term of this patent is extended or adjusted under 35 U.S.C. 154(b) by 0 days.

(21) Appl. No.: 09/991,753

(22) Filed: Nov. 26, 2001

(65) Prior Publication Data
US 2002/0061930 A1 May 23, 2002

Related U.S. Application Data

(63) Continuation of application No. 09/590,839, filed on Jun. 9, 2000, now abandoned.
(60) Provisional application No. 60/141,301, filed on Jun. 28, 1999.

(51) Int. Cl.[7] .......................... C07C 69/74; C07C 61/12
(52) U.S. Cl. .................. 560/122; 560/121; 562/504; 562/503; 562/498; 562/500; 562/501
(58) Field of Search ................... 560/122, 121; 562/504, 503, 498, 500, 501

(56) References Cited

FOREIGN PATENT DOCUMENTS

WO    WO99/33781    * 7/1999

OTHER PUBLICATIONS

Tetsuji Kametani et al, "Studies on the Syntheses of Heterocyclic Compounds–DCCLXII", Tetrahedron, vol. 37 (1981), pp. 715–719.

Ernest L. Eliel, "Stereochemistry of Carbon Compounds", McGraw–Hill Book Company, 1962, pp. 47–53.

Yarlagadda S. Babu et al, "Preparation of Substituted Cyclopentanes as Influenza Virus Neuraminidase Inhibitors", (WO97/47194), Chem. Abst. 128:101850 (1998).

Calvin A. Buehler et al, "Survey of Organic Syntheses", Wiley–Interscience, 1970, p. 818.

* cited by examiner

Primary Examiner—Alan L. Rotman
Assistant Examiner—Hector M Reyes
(74) Attorney, Agent, or Firm—Connolly Bove Lodge & Hutz LLP

(57) ABSTRACT

The invention relates to a process for preparing substituted cyclopentane derivatives represented by the formula (I)

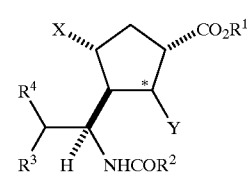

(I)

wherein $R^1$, $R^2$, $R^3$, $R^4$, X and Y are as described in the specification, and pharmaceutically acceptable salts thereof.

The invention further relates to a process for purifying the compound of formula (Ia)

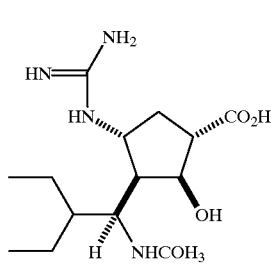

(Ia)

and novel crystalline forms of the compound of formula (Ia).

19 Claims, No Drawings

PROCESS FOR PREPARING SUBSTITUTED CYCLOPENTANE DERIVATIVES AND NOVEL CRYSTALLINE STRUCTURES THEREOF

CROSS REFERENCE TO RELATED APPLICATIONS

Continuation of application Ser. No. 09/590,839, filed on Jan. 9, 2000, now abandoned.

This application claims the benefit of U.S. Provisional Application No. 60/141,301, filed on Jun. 28, 1999.

BACKGROUND OF THE INVENTION

Field of the Invention

The invention relates to a process for preparing substituted cyclopentane derivatives represented by the formula (I)

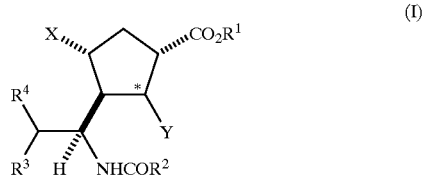

wherein $R^1$, $R^2$, $R^3$, $R^4$, X and Y are as described below, and pharmaceutically acceptable salts thereof.

The invention further relates to a process for purifying the compound of formula (Ia) and novel crystalline forms of the compound of formula (Ia).

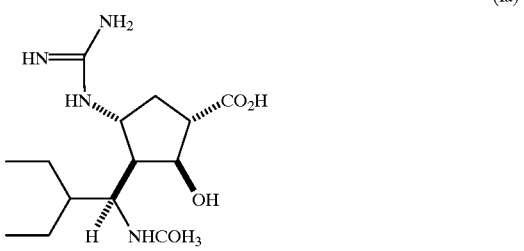

The compounds of formula (I) are neuraminidase inhibitors, useful for the treatment of influenza and other viral infections.

The compounds of formula (I) and method of making and using compounds of formula (I) are described in pending application PCT US 98/26871, filed Dec. 17, 1997.

The invention relates to a more efficient process of preparing the compounds of formula (I), more particularly a process which permits high yield isolation of the desired stereoisomer, without the need for chromatographic purification.

BRIEF SUMMARY OF THE INVENTION

The present invention relates to a process for preparing a compound of formula (I)

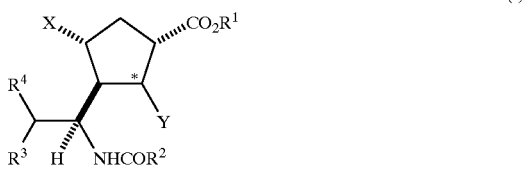

wherein $R^1$ is selected from the group consisting of hydrogen, alkyl, cycloalkyl, aryl and aralkyl;

$R^2$ is selected from the group consisting of hydrogen; alkyl, cycloalkyl, halogen substituted alkyl, aryl and substituted aryl;

$R^3$ and $R^4$ are independently selected from the group consisting of hydrogen, alkyl, alkylene, cycloalkyl, aryl and substituted aryl, provided that at least one of $R^3$ or $R^4$ is alkyl;

X is $NHC(=NH)NH_2$;

Y is selected from the group consisting of hydrogen, fluorine, hydroxy, $OR^5$, $OCOR^5$, $NH_2$, $NHCOR^5$ and $NR^5R^6$, where $R^5$ is selected from alkyl, aryl, $COR^6$ or $COOR^6$; and where $R^6$ is selected from hydrogen, alkyl, alkylene, cycloalkyl, aryl or substituted aryl;

and pharmaceutically acceptable salts thereof;

comprising the steps of:

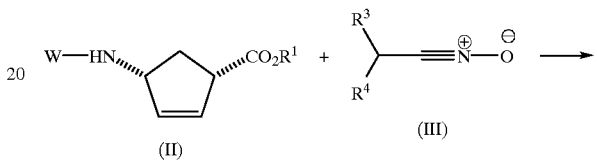

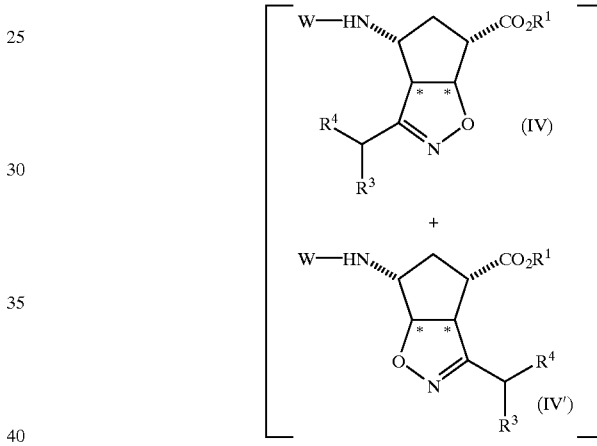

reacting a compound of formula (II), wherein W is an N-protecting group, with a nitrile oxide of formula (III) by cycloaddition, at a temperature which prevents uncontrolled decomposition of the compound of formula (III), to yield a mixture of two stereoisomers of two regioisomers of the formula (IV) and (IV'), respectively;

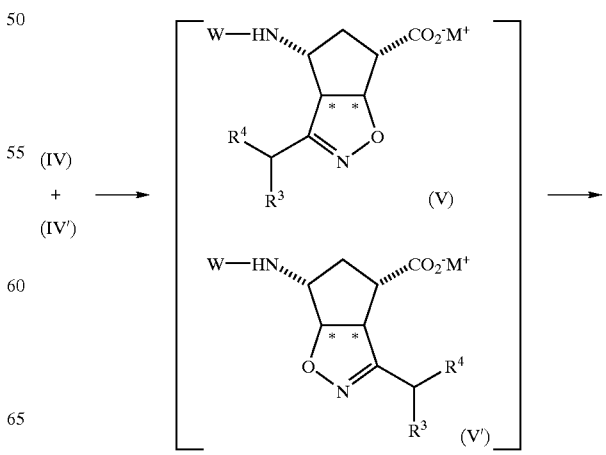

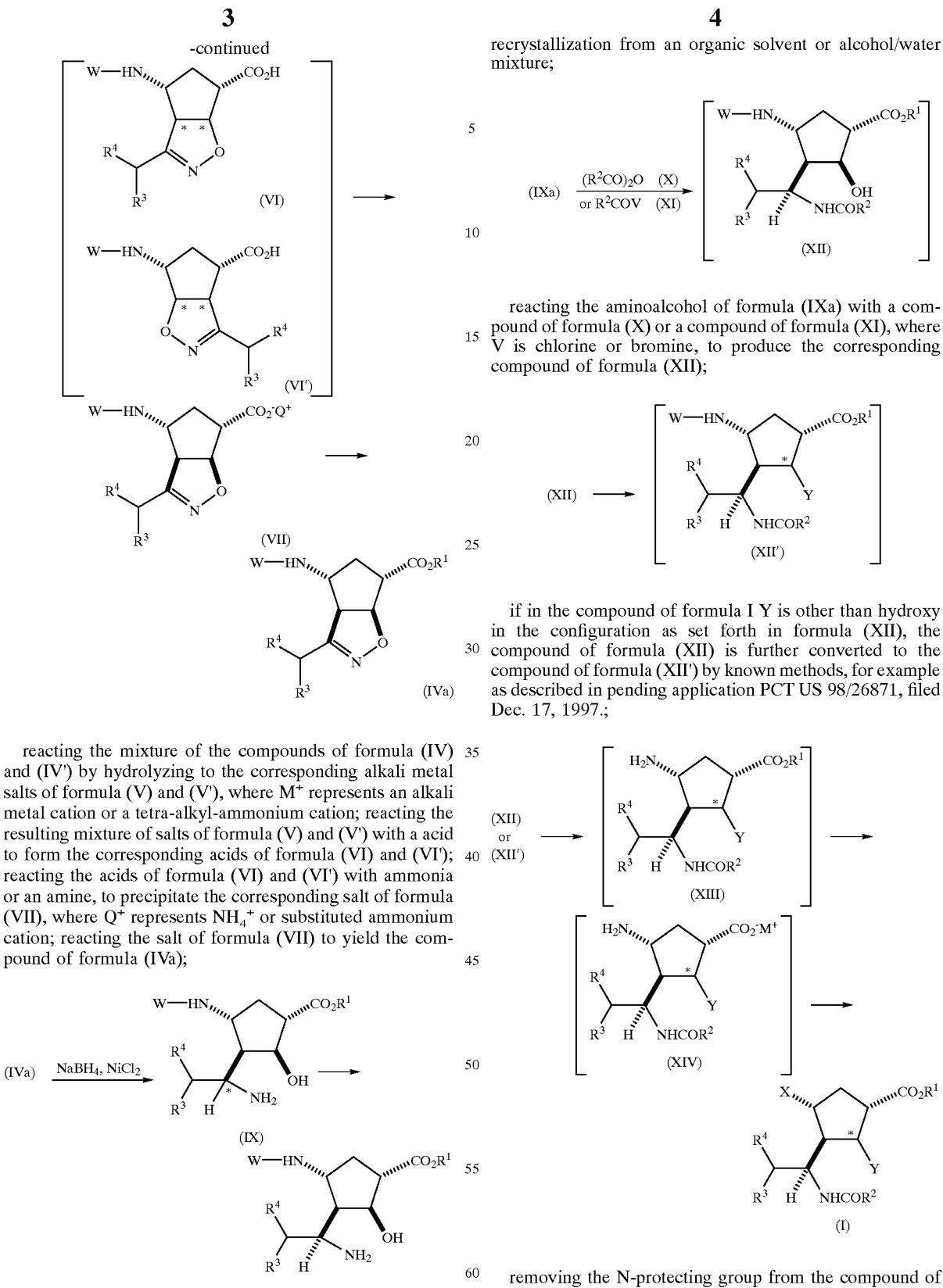

reacting the mixture of the compounds of formula (IV) and (IV') by hydrolyzing to the corresponding alkali metal salts of formula (V) and (V'), where $M^+$ represents an alkali metal cation or a tetra-alkyl-ammonium cation; reacting the resulting mixture of salts of formula (V) and (V') with a acid to form the corresponding acids of formula (VI) and (VI'); reacting the acids of formula (VI) and (VI') with ammonia or an amine, to precipitate the corresponding salt of formula (VII), where $Q^+$ represents $NH_4^+$ or substituted ammonium cation; reacting the salt of formula (VII) to yield the compound of formula (IVa);

reducing the compound of formula (IVa) using sodium borohydride and $NiCl_2$ to yield a mixture of two stereoisomers of the corresponding aminoalcohol of formula (IX); isolating the desired diastereomer of formula (IXa) by recrystallization from an organic solvent or alcohol/water mixture;

reacting the aminoalcohol of formula (IXa) with a compound of formula (X) or a compound of formula (XI), where V is chlorine or bromine, to produce the corresponding compound of formula (XII);

if in the compound of formula I Y is other than hydroxy in the configuration as set forth in formula (XII), the compound of formula (XII) is further converted to the compound of formula (XII') by known methods, for example as described in pending application PCT US 98/26871, filed Dec. 17, 1997.;

removing the N-protecting group from the compound of formula (XII) or (XII') to produce the corresponding amine of formula (XIII), or salt thereof; hydrolyzing the compound of formula (XIII) to the corresponding acid salt of formula (XIV); and reacting the compound of formula (XIV) with a guanylating agent, to produce the compound of formula (I).

For the compound of formula (XIII), if Y represents $NH_2$ or $NR^5R^6$ where $R^6$ is hydrogen, then Y is protected with a protecting group other than W, which protecting group is removed by known methods following the guanylation step.

In another aspect, the invention is directed to a recrystallization procedure for purification and formation of a stable crystalline form of the compound of formula (Ia)

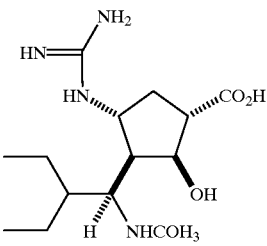
(Ia)

comprising the steps of dissolving the crude compound of formula (Ia) in a mixture of water/methanol at reflux temperature; and cooling to crystallize the pure compound of formula (Ia).

The process of this invention, as described herein, is advantageous over previously disclosed methods in that it does not require chromatographic separation or purification; it does not require the use of highly flammable or toxic solvents such as ether, $CH_2Cl_2$, and the like; and it results in high product yield and purity; making it suitable for large scale production.

The recrystallization as described above may be directed to produce either of two crystalline forms of the compound of formula (Ia), labelled Form A and Form B, or a mixture thereof.

A further aspect of the claimed invention is directed to novel crystalline structures of the compound of formula (Ia), more particularly Form A and Form B, characterized by their respective X-ray powder diffraction patterns.

Form A of the compound of formula (Ia) is more stable to changes in ambient relative humidity.

DETAILED DESCRIPTION OF THE INVENTION

As used herein, the term "alkyl" whether used alone or as part of a substituent group, include straight and branched chains containing one to eight carbon atoms, preferably one to three carbon atoms. For example, alkyl radicals include methyl, ethyl, propyl, isopropyl, butyl, isobutyl, sec-butyl, t-butyl, pentyl and the like.

As used herein, the term "alkylene" whether used alone or as part of a substituent group, include straight, branched or cyclic unsaturated hydrocarbon groups containing two to eight carbon atoms, preferably two to three carbon atoms. Examples of alkylene groups include vinyl, 1-propenyl, allyl, 2-propenyl, 2-methyl-1-propenyl, cyclopentenyl, and the like.

As used herein, unless otherwise noted, "cycloalkyl" shall denote cyclic aliphatic groups containing three to eight carbon atoms in the ring, optionally substituted with alkyl groups typically having one to six carbon atoms. Usually one or two substituent groups are present. Suitable examples of cycloalkyl groups include cyclopropyl, cyclobutyl, cyclopentyl, cyclohexyl, and the like.

As used herein, unless otherwise noted, "aryl" shall refer to unsubstituted carbocyclic aromatic groups containing six to fourteen carbon atom, such as phenyl, naphthyl, and the like, preferably phenyl.

As used herein, unless otherwise noted, "aralkyl" shall mean any alkyl group substituted with an aryl group. Suitable examples of aralkyl groups include benzyl, phenylethyl, and the like.

As used herein, unless otherwise noted, substituents on the aryl and aralkyl groups are one or more, preferably one or two, of halogen.

As used herein, "halogen" shall mean chlorine, bromine, fluorine and iodine.

As used herein, "amine" shall mean a primary, secondary or tertiary amine such as ethylamine, t-butylamine, dimethylamine, diethylamine, triethylamine, piperidine, morpholine, N-methyl morpholine, and the like.

As used herein, "guanylating agent" shall mean an agent which adds a formamidine group to an amine nitrogen. Suitable examples of a guanylating agent include formamidine sulfonic acid, S-methyl iso-thiourea, 1H-pyrazole-1-carboxamidine monohydrochloride, 1H-triazole-1-carboxamidine monohydrochloride, and the like. Preferably, the guanylating agent is 1H-pyrazole-1-carboxamidine monohydrochloride or 1H-triazole-1-carboxamidine monohydrochloride, more preferably 1H-triazole-1-carboxamidine monohydrochloride.

As used herein, unless otherwise noted, an N-protecting group shall mean any functional group that is bonded directly to the N and is capable of preventing reactions at the N. Such protecting groups are known in the art, for example as described in Protective Groups in Organic Chemistry, ed. J. F. W. McOmie, Plenum Press, 1973; and Protective Groups in Organic Synthesis, $3^{rd}$ Edition, T. W. Greene and P. G. M. Wuts, John Wiley & Sons, 1999. The appropriate choice of an N-protecting group can be made by one skilled in the art.

As used herein, the notation "*" shall denote the presence of a stereogenic center.

Where the compounds of the invention have one stereogenic center, they exist as enantiomers. Where the compounds possess two or more stereogenic centers, they additionally exist as diastereomers. It is to be understood that all such isomers and mixtures thereof are encompassed within the scope of the present invention.

With reference to substituents, the term "independently" means that when more than one of such substituents is possible, such substituents may be the same or different from each other.

As used herein, the term "a temperature which prevents uncontrolled decomposition" shall mean a temperature safely below the decomposition temperature. For example, when in the compound of formula (III), $R^3$ and $R^4$ are each ethyl, the temperature which prevents uncontrolled decomposition is $\leq 90°$ C.

Pharmaceutically acceptable salts of the compounds of formula (I) include those derived from pharmaceutically acceptable, inorganic and organic acids and bases. Examples of suitable acids include hydrochloric, hydrobromic, sulfuric, nitric, perchloric, fumaric, maleic, phosphoric, glycolic, lactic, salicylic, succinic, p-toluenesulfonic, tartaric, acetic, citric, methanesulfonic, formic, benzoic, malonic, naphthalene-2-sulfonic, trifluoroacetic and benzenesulfonic acids.

Salts derived from appropriate bases include alkali metal cations such as sodium, potassium, and the like; and ammonium ions such as ammonium, alkyl ammonium, and the like.

In a preferred embodiment, the claimed invention is used in preparing compounds of the formula (I) wherein $R^1$, $R^2$, $R^3$ and $R^4$ are independently selected from hydrogen or $C_1$–$C_4$ alkyl, $R^5$ is hydrogen and Y is OH. More preferably, the claimed invention is used to prepare the compound of formula (Ia).

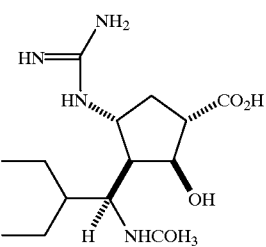
(Ia)

The present invention relates to a process for preparing a compound of formula (I) as illustrated in Scheme 1 below:
SCHEME 1
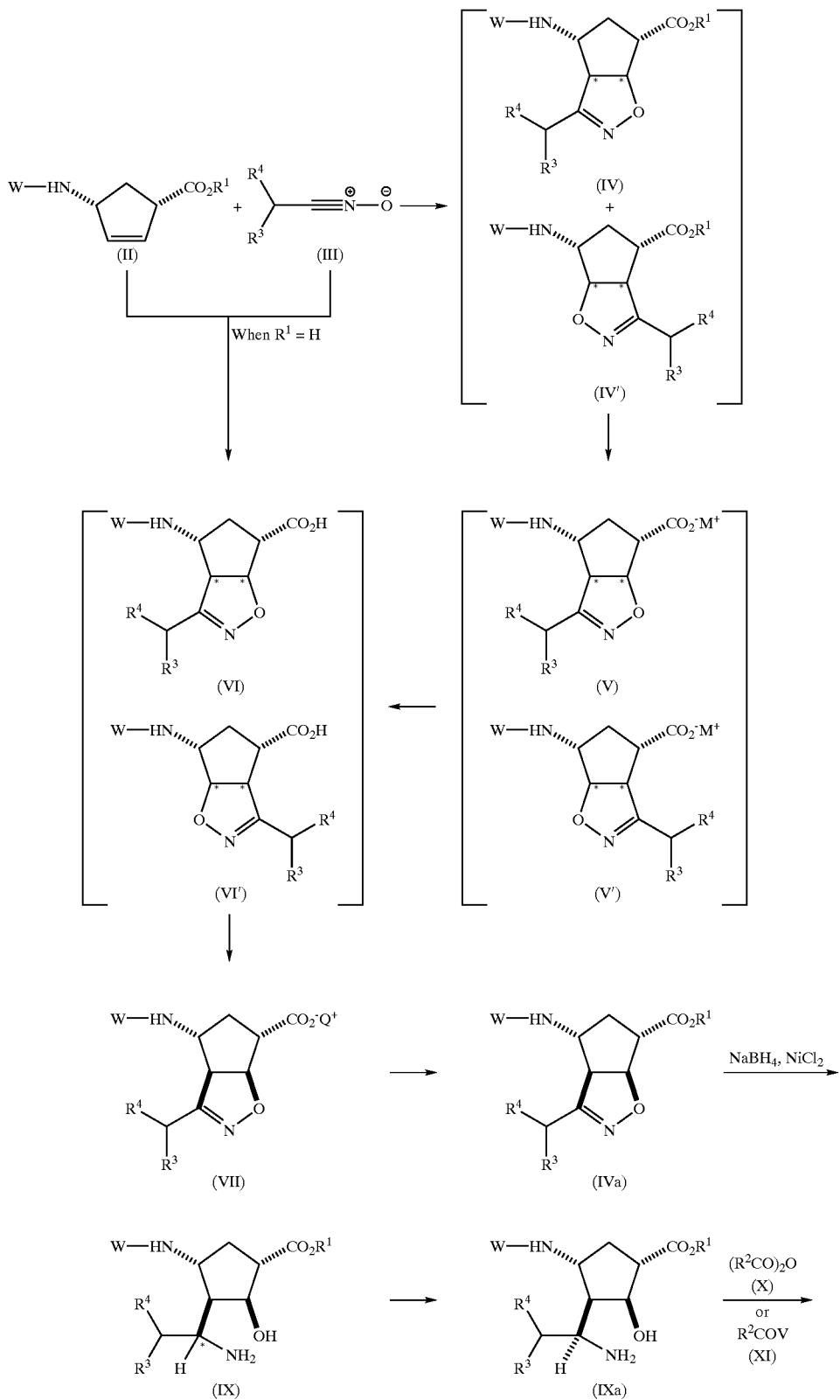

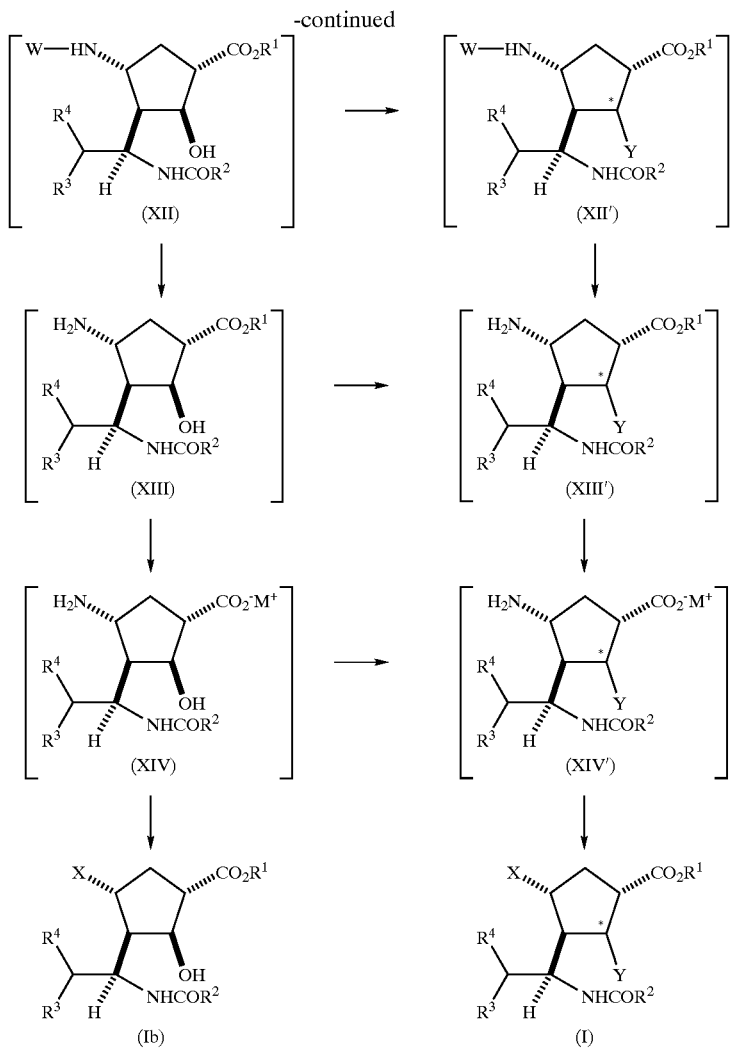

wherein $R^1$, $R^2$, $R^3$, $R^4$, X, Y, Q, V and W are as described above.

More particularly, an N-protected compound of formula (II), a known compound or compound prepared by known methods, is added to a nitrile oxide of formula (III), a compound prepared in situ by known methods, by cycloaddition in an inert organic solvent such as toluene, benzene, xylene, cyclohexane and the like, at a temperature which prevents uncontrolled decomposition of the compound of formula (III), preferably at a temperature between about 40° C. and about 90° C., in the presence of a tertiary amine such as triethylamine, diisopropylethylamine, N-methylmorpholine, and the like, preferably triethylamine, to yield a mixture of two stereoisomers of two regioisomers of formula (IV) and (IV')

The substituted nitrile oxide of formula (III) can be produced in situ by known methods, preferably by heating a suitably substituted chlorooxime (represented by the formula $R^3R^4CH-C(Cl)=NOH$). For example, as described in Curran, D. P. & Gothe, S. A., Tetrahedron, 1988, 44(13), 3945–52.

To selectively isolate the desired stereoisomer, that is the compound of formula (IVa), the mixture of (IV) and (IV'), present in the organic solvent, is hydrolyzed with a basic aqueous solution, such as sodium hydroxide, potassium hydroxide and the like, preferably sodium hydroxide, to produce a mixture of the corresponding alkali metal salts of formula (V) and (V'), respectively. The aqueous phase (containing the alkali metal salts) is separated from the organic phase and mixed with a suitable solvent such as an organic ether, for example methyl tert-butyl ether; an organic ester, for example ethyl acetate; a hydrocarbon, for example toluene; a water immiscible ketone, for example methyl-isobutyl ketone; or a water immiscible alcohol, for example n-butanol; preferably the solvent is methyl tert-butyl ether. The resulting mixture is treated with an acid, such as acetic, hydrochloric, sulfuric, and the like, preferably hydrochloric, to a pH of about 3–5, preferably to a pH of about 4, to produce the corresponding acids of formula (VI) and (VI'). The organic phase is separated and treated with ammonia or an amine, preferably t-butyl amine, preferably at a temperature between about 15–30° C., more preferably at room temperature (20–25° C.), resulting in precipitation of the corresponding salt, a compound of formula (VII), where $Q^+$ represents $NH_4^+$ or substituted ammonium cation.

Alternatively, the reaction mixture containing the compounds of formula (V) and (V') is acidified with an acid, such as acetic, hydrochloric, sulfuric, and the like, preferably hydrochloric, to a pH in the range of about 0.5–3, preferably to a pH in the range of about 1–2, to produce the corresponding compounds of formula (VI) and (VI'). The organic phase is then separated and treated with ammonia or an organic amine, preferably t-butylamine, preferably at a temperature between about 15–30° C., more preferably at room temperature, to produce the corresponding compound of formula (VII) as a precipitate, wherein $Q^+$ is as previously defined.

If in the compound of formula (II), $R^1$ is hydrogen, then the compound of formula (II) is reacted with the compound of formula (III), under the above described conditions, to produce the compounds of formula (VI) and (VI') directly.

The salt of formula (VII) is suspended in an alcohol of the formula $R^1OH$, a compound of formula (VIII), preferably treated with a corresponding orthoester. The resulting suspension is treated with a strong non-aqueous acid such as gaseous HCl, gaseous HBr, perchloric acid, p-toluene sulfonic, and the like, preferably gaseous HCl, at a temperature $\leq 20°$ C., resulting in formation of the compound of formula (IVa). If the N-protecting group on the compound of formula (VII) is t-butoxycarbonyl (Boc), the solution is further treated with di-tert-butyl dicarbonate (Boc anhydride) and a tertiary amine such as triethylamine, diisopropylethylamine, N-methylmorpholine, and the like, preferably triethylamine.

Alternatively, if the N-protecting group on the compound of formula (VII) is t-butoxycarbonyl (Boc), the compound of formula (VII) is suspended in an organic solvent such as acetone, 2-butanol, acetonitrile, and the like, preferably acetone, and then treated with a base such as potassium carbonate, sodium carbonate, and the like, or an alkali hydroxide such sodium hydroxide, potassium hydroxide, and the like, or a mixture thereof, preferably a mixture thereof such as a mixture of sodium hydroxide and sodium carbonate. Preferably, the resulting suspension is heated to remove the amine byproduct of $Q^+$, and then treated with an alkylating agent such as an alkyl halide, dimethyl sulfate, and the like, preferably dimethyl sulfate, to yield the corresponding compound of formula (Iva).

The stereoisomer of formula (IVa) is reduced to the corresponding compound of formula (IX) using sodium borohydride, preferably in the range of about 2–3 molar equivalents, and nickel chloride, preferably in an amount equal to at least 1 molar equivalent, in an alcohol such as methanol, ethanol, and the like, preferably in an alcohol of formula (VIII), preferably at a temperature of less than 10° C. The product is isolated by addition of sodium nitrite, ammonium hydroxide and ammonium chloride, resulting in precipitation of the corresponding aminoalcohol of formula (IX).

The desired diastereomer of the compound of formula (IXa) is isolated by recrystallization from an organic solvent such as toluene, ethyl acetate, and the like; or alcohol/water mixture such as methanol/water, ethanol/water, and the like; preferably toluene.

Alternatively, the desired diastereomer of formula (IXa) is isolated by dissolving the mixture of formula (IX) in a weak acidic aqueous solution such as aqueous hydrochloric acid, acetic acid, and the like, adjusting the pH of the solution to pH>7 with ammonium hydroxide, and extracting with an organic solvent such as ethyl acetate. The compound of formula (IXa) is then isolated by known methods.

The aminoalcohol of formula (IXa) is reacted with a compound of formula (X) or a compound of formula (XI), preferably a compound of formula (X), preferably with 1 to 2 equivalents, more preferably about 1 equivalent, in an inert organic solvent such as toluene, ethyl acetate, and the like, preferably toluene, to yield the corresponding compound of formula (XII).

If in the compound of formula (I) Y is other than hydroxy in the configuration as set forth in formula (XII), the compound of formula (XII) is further converted to the compound of formula (XII') by known methods, for example as described in pending application PCT US 98/26871, filed Dec. 17, 1997;

The N-protecting group on the compound of formula (XII) or (XII') is removed by known methods, to produce the corresponding amine of formula (XIII) or (XIII'), respectively, or salts thereof, which amines or salts thereof are present in their dissolved forms within the separated aqueous phase.

When the N-protecting group on the compound of formula (XII) or (XII') is Boc, the N-protecting group is removed by treating the compound of formula (XII) or (XII'), present in an organic solvent, with an acid such as aqueous hydrochloric or aqueous hydrobromic, preferably aqueous hydrochloric, at a pH in the range of 0–3, preferably to a pH<1, more preferably to a pH 0, preferably at a temperature in the range of 0–20° C., to produce the salt of the corresponding amine of formula (XIII) or (XIII'), respectively.

To the separated aqueous phase containing the compound of formula (XIII) or (XIII') is added a base, such as aqueous sodium hydroxide, aqueous potassium hydroxide, and the like, to adjust the pH to between about 6–13, preferably to a pH of 12–13, preferably at a temperature of less than or equal to about 10° C., resulting in the compound of formula (XIV) or (XIV'), respectively. To the solution containing the compound of formula (XIV) or (XIV') is added a guanylating agent, at a pH in the range of 7.5–14, preferably in the range of 8–10, at a temperature in the range of 0–90° C., preferably at a temperature in the range of 10–50° C., to yield the compound of formula (Ib) or (I), respectively.

Preferably, the guanylating agent is 1H-pyrazole-1-carboxamidine monohydrochloride, added at a pH about 9.5, at a temperature in the range of 40–50° C.; or 1H-triazole-1-carboxamidine monohydrochloride, added at a pH about 8.5, at a temperature in the range of 20–30° C. More preferably the guanylating agent is 1H-triazole-1-carboxamidine monohydrochloride.

Alternatively, the compound of formula (XII) may be hydrolyzed prior to removal of the protecting group.

If in the compound of formula (I) $R^1$ is other than hydrogen, the separated aqueous phase containing the compound of formula (XIII) or (XIII') is treated directly with a guanylating agent, at a pH in the range of 7.5–14, preferably in the range of 8–10, at a temperature in the range of 0–90° C., preferably at a temperature in the range of 10–50° C., to yield the corresponding compound of formula (Ib) or (I), respectively.

The compound of formula (Ia) is purified by dissolving the crude product in a mixture of methanol:water, preferably in the range of 5:95 to 50:50, more preferably 10:90, at reflux temperature. Preferably, the solution is maintained at reflux until the boiling temperature reaches between about 85°–100° C., more preferably 98–100° C. The resulting solution is cooled to precipitate the purified product of formula (Ia).

Recrystallization of the compound of formula (Ia) as described above will yield one of two novel crystalline forms, Form A or Form B, or a mixture thereof. Form A is obtained by slow recrystallization from the water/methanol solution, where the volume of the solution is $\geq 7$ mL/g, preferably >10 mL/g, preferably where initial precipitation occurs at $\leq 30°$ C. Form B is obtained by more rapid recrystallization from the water/methanol solution, where the volume of solution is ≦7 mL/g, preferably where initial precipitation occurs at >30° C. Form B or a mixture of Form A and Form B can be completely converted to Form A by stirring the solid in water, preferably at a temperature of ≧20° C., more preferably at a temperature of about 70–80° C., and preferably cooling to a temperature of about 0–5° C.

Preferably, Form A is prepared by rapid recrystallization of the compound of formula (Ia) to produce Form B or a mixture of Form A and Form B, followed by complete conversion to Form A.

The novel crystalline forms of the compound of formula (Ia) may be characterized by their respective x-ray powder diffraction patterns utilizing a Philips PW3710 based powder diffractometer using $CuK_{\alpha}$ radiation and the following system conditions:

| | |
|---|---|
| a) | CuKα radiation, 30 mA, 40 KV |
| b) | Optics |
| | 1/12° divergence slit |
| | 0.2 receiving slit |
| c) | Scan 4 to 35° 2θ at a scan rate of 0.016° 2θ/second |
| d) | Aluminum sample holder |

Form A of the compound of formula (Ia) appears as small, high density shiny crystals, may exist as a di- or tri-hydrate and may be characterized by its X-ray diffraction pattern:

FORM A-POWDER X-RAY DIFFRACTION RESULTS

| Angle° 2θ | d Spacing (Å) | Relative Intensity |
|---|---|---|
| 4.27 | 20.70 | 16.1 |
| 4.74 | 18.65 | 100.0 |
| 6.08 | 14.54 | 43.0 |
| 6.49 | 13.62 | 26.2 |
| 7.61 | 11.61 | 19.9 |
| 7.70 | 11.47 | 18.5 |
| 9.01 | 9.81 | 20.7 |
| 9.30 | 9.50 | 65.0 |
| 9.41 | 9.40 | 32.3 |
| 10.09 | 8.76 | 2.8 |
| 11.08 | 7.98 | 1.7 |
| 11.96 | 7.40 | 23.5 |
| 12.08 | 7.32 | 28.0 |
| 12.43 | 7.12 | 8.3 |
| 12.88 | 6.87 | 32.1 |
| 13.00 | 6.81 | 30.7 |
| 13.28 | 6.66 | 19.9 |
| 13.92 | 6.36 | 24.4 |
| 14.06 | 6.30 | 13.8 |
| 15.17 | 5.84 | 69.4 |
| 15.33 | 5.78 | 51.5 |
| 16.60 | 5.34 | 20.0 |
| 17.18 | 5.16 | 11.8 |
| 18.62 | 4.76 | 35.4 |
| 18.81 | 4.71 | 21.2 |
| 19.62 | 4.52 | 47.0 |
| 20.11 | 4.41 | 46.5 |
| 20.27 | 4.38 | 47.3 |
| 20.76 | 4.28 | 42.3 |
| 21.33 | 4.16 | 25.8 |
| 21.85 | 4.06 | 22.5 |
| 22.88 | 3.88 | 27.5 |
| 23.77 | 3.74 | 43.2 |
| 24.20 | 3.68 | 58.9 |
| 24.81 | 3.59 | 31.3 |
| 26.23 | 3.40 | 46.3 |
| 26.50 | 3.36 | 47.7 |
| 27.25 | 3.27 | 26.7 |
| 27.83 | 3.20 | 45.3 |
| 28.60 | 3.12 | 23.0 |
| 29.56 | 3.02 | 33.3 |
| 30.50 | 2.93 | 41.1 |
| 30.76 | 2.90 | 38.9 |
| 31.28 | 2.86 | 29.5 |
| 31.95 | 2.80 | 21.8 |
| 33.63 | 2.66 | 29.2 |
| 34.26 | 2.62 | 20.2 |

Form A of the compound of formula (Ia) may be characterized by an X-ray diffraction pattern comprising the following major peaks:

FORM A-POWDER X-RAY DIFFRACTION MAJOR PEAKS

| Angle° 2θ | d Spacing (Å) | Relative Intensity |
|---|---|---|
| 4.74 | 18.65 | 100.0 |
| 6.08 | 14.54 | 43.0 |
| 6.49 | 13.62 | 26.2 |
| 7.61 | 11.61 | 19.9 |
| 9.30 | 9.50 | 65.0 |
| 10.09 | 8.76 | 2.8 |
| 11.08 | 7.98 | 1.7 |
| 12.08 | 7.32 | 28.0 |
| 13.00 | 6.81 | 30.7 |
| 13.92 | 6.36 | 24.4 |
| 15.17 | 5.84 | 69.4 |
| 16.60 | 5.34 | 20.0 |
| 17.18 | 5.16 | 11.8 |
| 18.62 | 4.76 | 35.4 |
| 19.62 | 4.52 | 47.0 |
| 20.11 | 4.41 | 46.5 |
| 20.76 | 4.28 | 42.3 |
| 21.85 | 4.06 | 22.5 |
| 22.88 | 3.88 | 27.5 |
| 23.77 | 3.74 | 43.2 |
| 24.20 | 3.68 | 58.9 |
| 24.81 | 3.59 | 31.3 |
| 26.50 | 3.36 | 47.7 |
| 27.83 | 3.20 | 45.3 |
| 28.60 | 3.12 | 23.0 |
| 29.56 | 3.02 | 33.3 |
| 30.50 | 2.93 | 41.1 |
| 31.28 | 2.86 | 29.5 |
| 31.95 | 2.80 | 21.8 |
| 33.63 | 2.66 | 29.2 |
| 34.26 | 2.62 | 20.2 |

Form B of the compound of formula (Ia) appears as fluffy, low density needles, exists as a di-hydrate and may be characterized by its X-ray diffraction pattern:

FORM B-POWDER X-RAY DIFFRACTION RESULTS

| Angle° 2θ | d Spacing (Å) | Relative Intensity |
|---|---|---|
| 8.90 | 9.93 | 25.2 |
| 10.00 | 8.84 | 35.6 |
| 10.17 | 8.70 | 72.9 |
| 10.48 | 8.43 | 9.7 |
| 12.59 | 7.03 | 44.1 |
| 12.79 | 6.92 | 35.6 |
| 13.76 | 6.43 | 2.3 |
| 14.52 | 6.10 | 62.5 |

FORM B-POWDER X-RAY DIFFRACTION RESULTS
-continued

| Angle° 2θ | d Spacing (Å) | Relative Intensity |
| --- | --- | --- |
| 14.65 | 6.04 | 92.8 |
| 15.47 | 5.73 | 9.7 |
| 15.59 | 5.68 | 9.5 |
| 17.31 | 5.12 | 9.4 |
| 17.94 | 4.94 | 36.7 |
| 19.41 | 4.57 | 4.2 |
| 20.39 | 4.35 | 32.8 |
| 20.59 | 4.31 | 36.1 |
| 21.18 | 4.19 | 1.4 |
| 22.70 | 3.91 | 100.0 |
| 23.30 | 3.82 | 23.7 |
| 23.62 | 3.76 | 32.1 |
| 24.00 | 3.70 | 14.6 |
| 24.56 | 3.62 | 26.2 |
| 25.32 | 3.52 | 10.6 |
| 25.88 | 3.44 | 42.6 |
| 26.18 | 3.40 | 9.1 |
| 27.04 | 3.30 | 19.0 |
| 28.43 | 3.14 | 30.4 |
| 28.83 | 3.09 | 23.1 |
| 29.33 | 3.04 | 16.2 |
| 29.43 | 3.03 | 14.2 |
| 31.53 | 2.84 | 12.0 |
| 31.87 | 2.81 | 12.1 |
| 32.08 | 2.79 | 12.5 |
| 32.86 | 2.72 | 15.3 |
| 33.44 | 2.68 | 18.5 |

Form B of the compound of formula (Ia) may be characterized by an X-ray diffraction pattern comprising the following major peaks:

FORM B-POWDER X-RAY DIFFRACTION MAJOR PEAKS

| Angle° 2θ | d Spacing (Å) | Relative Intensity |
| --- | --- | --- |
| 8.90 | 9.93 | 25.2 |
| 10.17 | 8.70 | 72.9 |
| 10.48 | 8.43 | 9.7 |
| 12.59 | 7.03 | 44.1 |
| 12.79 | 6.92 | 35.6 |
| 13.76 | 6.43 | 2.3 |
| 14.65 | 6.04 | 92.8 |
| 15.59 | 5.68 | 9.5 |
| 17.31 | 5.12 | 9.4 |
| 17.94 | 4.94 | 36.7 |
| 19.41 | 4.57 | 4.2 |
| 20.59 | 4.31 | 36.1 |
| 22.70 | 3.91 | 100.0 |
| 23.30 | 3.82 | 23.7 |
| 23.62 | 3.76 | 32.1 |
| 24.56 | 3.62 | 26.2 |
| 25.88 | 3.44 | 42.6 |
| 27.04 | 3.30 | 19.0 |
| 28.43 | 3.14 | 30.4 |
| 28.83 | 3.09 | 23.1 |
| 29.33 | 3.04 | 16.2 |
| 31.53 | 2.84 | 12.0 |
| 31.87 | 2.81 | 12.1 |
| 32.86 | 2.72 | 15.3 |
| 33.44 | 2.68 | 18.5 |

The following examples describe the invention in greater detail and are intended to illustrate the invention, but not to limit it.

EXAMPLE 1
Preparation of 2-Ethyl-N-hydroxybutanimidoyl Chloride

Hydroxylamine hydrochloride (230.1 g, 3.31 mol) was dissolved in purified water (220 g). Toluene (740 g) was added, followed by addition of 2-Ethylbutyraldehyde (315.6 g, 3.15 mol). The two-phase mixture was stirred vigorously while cooling. Sodium hydroxide solution (ca. 30%, 463 g, 3.47 mol) was added slowly over about 1 h. (Addition is very exothermic) to maintain a temperature between 15–25° C. The mixture was stirred for an additional 30–60 min, then allowed to stand to separate the layers. The organic layer, containing the oxime, was used in the next step without further treatment.

N-Chlorosuccinimide (NCS) (421.2 g, 3.15 mol) was suspended in dimethylformamide (DMF) (499.4 g) and cooled to about 10° C. The oxime solution in toluene (3.15 mol) was added slowly over at least 2 h with sufficient cooling to maintain the reaction temperature between 10–25° C. (The reaction is exothermic, but heat evolution is not immediate. Initially small amounts of the oxime solution (about 5%) were added. Once heat evolution began, the remainder of the solution was added). After complete addition of the oxime, the mixture was stirred at 15–25° for at least 30 min. Purified water (1050 g) was added slowly (slight exothermic) over 15 min while maintaining the temperature at 10–30° C. The two-phase mixture was stirred for 15 min. at 15–25° C. and the layers were separated. The water layer was discarded and the organic layer washed with purified water (3×1050 g). The organic layer containing the chlorooxime was isolated and used in the next step without further purification. (The solution is lachrymator).

EXAMPLE 2
(3aR,4R,6S,6aS)-2,2-Dimethylethylammonium 4-[[(1,1-dimethylethoxy)carbonyl]amino]-3-(1'-ethylpropyl)-3a,5,6,6a-tetrahydro-4H-cyclopent[d]isoxazole-6-carboxylate (1S, 4R)-(−)-Methyl-[[(1,1-dimethylethoxy)carbonyl] amino]cyclopent-2-ene-1-carboxylate (50 g, 0.207 mol) was dissolved in toluene (310 g) and triethylamine (62.9 g, 0.622 mol) and the reaction mixture was heated to 60–70° C. 2-Ethyl-N-hydroxybutanimidoyl chloride (93.0 g, 0.622 mol) in toluene (130 g) was added over 2.5 h to the above solution. A white solid precipitated (triethylammonium chloride). After complete addition, the reaction mixture was stirred for an additional 5 h at 60–70° C. The reaction mixture was cooled to 20–25° C., the precipitate was removed by filtration and the filter cake was washed with toluene (50 g). The combined filtrate was treated with a solution of sodium hydroxide (12.4 g, 0.311 mol) in water (37.3 g) at 15° C. The temperature was increased slowly to about 30° C. The reaction mixture was diluted with water (294 g), and the phases were separated. The organic phase was extracted with water (50 g) and the combined aqueous phases were extracted with toluene (50 g). tert-Butyl methyl ether (250 g) was added to the aqueous phase, and the pH of the mixture was adjusted to 4.0 by addition of concentrated HCl (26.1 g, 0.265 mol). The phases were separated, and the aqueous phase was extracted with tert-butyl methyl ether (250 g). The combined organic phases were dried over magnesium sulfate (20 g). The drying agent was filtered off, and rinsed with tert-butyl methyl ether (50 g). The combined filtrate was diluted with tert-butyl methyl ether (250 g), and treated with tert-butylamine (15.2 g, 0.207 mol) at 20–25° C. The product precipitated as a white solid. The mixture was stirred for 3 h, then the precipitate was collected by filtration, rinsed with tert-butyl methyl ether (75 g) and dried for 16 h at 40° C.

Yield 56.68 g (66%), purity (LC) >98%.

EXAMPLE 3
(3aR,4R,6S,6aS)-(+)-Methyl 4-[[(1,1-dimethylethoxy)carbonyl]amino]-3-(1'-ethylpropyl)-3a,5,6,6a-tetrahydro-4H-cyclopent[d]isoxazole-6-carboxylate (3aR,4R,6S,6aS)-1,1-dimethylethylammonium 4-[[(1,1-dimethylethoxy)carbonyl]amino]-3-(1'-ethylpropyl)-4,5,6, 6a-tetrahydro-3aH-cyclopent[d]isoxazole-6-carboxylate (100 g, 0.242 mol) was suspended in methanol (200 g). Trimethylorthoformate (30.8 g, 0.290 mol) was added, and the reaction mixture was cooled to 10–20° C. HCl gas (11.0 g, 0.302 mol) was bubbled into the reaction mixture over 15 min (maximum temperature 20° C.); the mixture became a clear solution. The solution was stirred for 2–3 h at 18–25° C. Di-tert-butyl dicarbonate (BOC-anhydride) (13.2 g, 0.06 mol) was added and stirred for 5 min, triethylamine (9.0 g, 0.089 mol) was then added to adjust the pH to between 8–9. The solution was stirred for 15–30 min, then cooled to 12–18° C., and diluted with water (120 g). The solution was seeded and stirred for 15–30 min, while the product started to precipitate. Additional water (200 g) was added, the suspension was cooled to 0–5° C. and stirred for an additional 1–2 h. The product was collected by filtration, washed with water (150 g) and dried in vacuo at 45–50° C.

Yield 82.82 g (96.6%), purity (LC) 99.2%.

EXAMPLE 4

(1S,2S,3S,4R,1'S)-Methyl 3-[(1'-amino-2'-ethyl) butyl]-4-[[(1,1-dimethylethoxy) carbonyl]amino]-2-hydroxycyclopentane-1-carboxylate (3aR,4R,6S,6aS)-(+)-Methyl 4-[[(1,1-dimethylethoxy) carbonyl]amino]-3-(1'-ethylpropyl)-3a, 5,6,6a-tetrahydro-4H-cyclopent [d]isoxazole-6-carboxylate (100 g, 0.282 mol) and nickel chloride hexahydrate (70.4 g, 0.296 mol) were dissolved in methanol (254 g). The green solution was cooled to 0–5° C., while a suspension formed. Sodium hydroxide (0.5 g, 0.011 mol) and sodium borohydride (28.0 g, 0.741 mol) were dissolved in methanol (228 g) and added over 4 h to the reaction mixture at 0–10° C. (reaction is highly exothermic). A black suspension was formed along with strong gas formation. After complete addition of the borohydride solution, the reaction mixture was stirred for 30 min at 0–5° C. A solution of sodium nitrite (20 g, 0.291 mol), ammonium chloride (56.1 g, 1.05 mol), and 25% aq. ammonium hydroxide (65 g, 0.954 mol) in water (639 g) was added at a rate that maintained the reaction temperature at or below 25° C. The black solid dissolved and a thick bluish suspension was formed. The mixture was stirred for 12–16 h at 20–25° C. The precipitate was collected by filtration and washed twice with a solution of 25% aq. ammonium hydroxide (136 g) in water (864 g) to yield wet crude product (300 g). The wet crude product was suspended in toluene (1500 g) and 25% aq. ammonium hydroxide (150 g). The suspension was heated to 70–80° C. for 30–60 min. A clear two-phase system was obtained. The phases were separated, and 25% aq. ammonium hydroxide (150 g) was added to the organic phase. After heating to 70–80° C. the phases were separated, and a solution of ethylene diamine tetraacetic acid (EDTA) disodium salt dihydrate (150 g) in water (200 g) was added. After heating for 30–60 min to 70–80° C., the phases were separated and the organic layer was cooled to 0–5° C. over 2–3 h. A jelly-like suspension was formed. After stirring for an additional 2–3 h at 0–5° C., the product was collected by filtration and rinsed with toluene (200 g). The wet product was dried in vacuo at 40–50° C.

Yield 74.0 g (73.2%), purity (LC) 98.2%.

EXAMPLE 5

(1S,2S,3R,4R,1'S)-(−)-3-[(1'-Acetylamino-2'-ethyl) butyl]-4-[[(aminoimino)methyl]amino]-2-hydroxycyclopentan-1-carboxylic Acid (1S,2S,3S,4R,1'S)-Methyl 3-[(1'-amino-2'-ethyl)butyl]-4-[[(1,1-dimethylethoxy) carbonyl]amino]-2-hydroxycyclopentane-1-carboxylate (21.16 g, 0.060 mol) was suspended in toluene (88.7 g) and cooled to 0–5° C. Acetic anhydride (7.02 g, 0.069 mol) was added over 10 min at 0–30° C. The reaction mixture was stirred for 1 h at room temperature and then extracted with a solution of sodium carbonate (5.0 g, 0.047 mol) in water (50 g). The aqueous phase was discarded, the organic phase was added over 5 min to 37 wt % hydrochloric acid (23.2 g, 0.235 mol) at 0–5° C. Gas evolution was observed. Gas evolution decreased after 15 min. After stirring for 1 h at 0–10° C., the layers were separated, and the organic layer was washed with water (10 g). The combined aqueous layers were treated with a 30 wt % solution of sodium hydroxide (a total of 36.1 g, 0.271 mol) in water, added slowly at 0–10° C. under pH-control. The pH was adjusted to 12.5. Initially, the pH decreased quickly, and sodium hydroxide solution had to be added to maintain this pH value. After 45 min, the pH became constant at 12.5. The solution was stirred for an additional 30 min at 0–10° C. 1,2,4-Triazole-1-formamidine hydrochloride (10.78 g, 0.073 mol) was added at 0–30° C. The suspension was stirred for 15 min and the pH was adjusted to 8.4 by adding 30% aqueous sodium hydroxide solution (1.0 g, 0.08 mmol). A clear solution was formed. After about 2 h a white solid started to precipitate. The reaction mixture was stirred at room temperature overnight while the pH increased to 8.5. The suspension was cooled to 0–5° C. and stirred for additional 2–3 h. The product was collected by filtration, and washed with water (10 g). The product is either air-dried or used as a wet cake for the recrystallization step.

EXAMPLE 6

Recrystallization of (1S,2S,3R,4R,1'S)-(−)-3-[(1'-Acetylamino-2'-ethyl)butyl]-4-[[(aminoimino) methyl]amino]-2-hydroxycyclopentan-1-carboxylic Acid Crude (1S,2S, 3R, 4R, 1'S)-(−)-3-[(1'-Acetylamino-2'-ethyl)butyl]-4-[[(aminoimino)methyl]amino]-2-hydroxycyclopentan-1-carboxylic acid (97.0 g, 0.273 mol, a 1.5 hydrate) was mixed with distilled water (600 mL) and methanol (70 mL). The mixture was heated to boiling until the solid dissolved. The solution was hot filtered to remove any dust or insoluble particles. Heating was continued from an initial boiling point of 84° C. until the boiling point reached 99–100° C., resulting in distillation of the methanol, to a final solution volume of about 6 ml/g. The mixture was cooled to room temperature, during which time the product precipitated as white needles of crystalline Form B. The mixture was stirred overnight at room temperature. The solid was then collected by filtration, rinsed with cold (5–10° C.) water (50 mL) and air dried to yield Form A product as a white solid/crystals. Yield of isolated solid: 88.5 g (84.7% of theory) mp 256–258° C. (decomposition). A second crop (8.5 g, 8%) was obtained after concentration of mother liquor to 250 mL and stirring overnight.

EXAMPLE 7

(3aR,4R,6S,6aS)-1,1-Dimethylethylammonium 4-[[(1,1-dimethylethoxy) carbonyl]amino]-3-(1'-ethylpropyl)-3a,5,6,6a-tetrahydro-4H-cyclopent[d] isoxazole-6-carboxylate A solution of (3aR,4R,6S,6aS)-(+)-Methyl 4-[[(1,1-dimethylethoxy)carbonyl]amino]-3-(1'-ethylpropyl)-3a,5,6,6a-tetrahydro-4H-cyclopent [d] isoxazole-6-carboxylate and its diastereoisomers in toluene (1943 g, 0.73 mol) was treated with a solution of sodium hydroxide (46 g, 1.15 mol) in water (300 g) at 20–25° C. The two phase system was stirred for 2.5–3.5 h. 37 wt % hydrochloric acid (142.9 g, 1.45 mol) dissolved in water (257 g) was added within 30 min. The phases were separated, and the acidic aqueous phase was discarded. The organic phase was treated with tert-butylamine (62.17 g, 0.85 mol) at 20–40° C. The product precipitated as a slightly yellow solid. The reaction mixture was heated to reflux, the resulting suspension was stirred at 90–100° C. for 2.5 h, then cooled to 20–25° C. over 2 h, and stirred for a further 60 min. The precipitate was collected by filtration, rinsed with acetone (500 g) and dried for 12 h at 50° C.

Yield 286.24 g (67.4%), purity (LC) >97%.

EXAMPLE 8

(3aR,4R,6S,6aS)-(+)-Methyl 4-[[(1,1-dimethylethoxy)carbonyl]amino]-3-(1'-ethylpropyl)-3a,5,6,6a-tetrahydro-4H-cyclopent[d]isoxazole-6-carboxylate (3aR,4R,6S,6aS)-1,1-dimethylethylammonium 4-[[(1,1-dimethylethoxy)carbonyl]amino]-3-(1'-ethylpropyl)-4,5,6,6a-tetrahydro-3aH-cyclopent[d]isoxazole-6-carboxylate (422 g, 1.0 mol) was suspended in methanol (500 g). Trimethylorthoformate (137.96 g, 1.3 mol) was added, and the reaction mixture was cooled to 10–15° C. A solution of HCl gas (6.0 mol/L) in methanol (216.7 g, 1.3 mol) was added over 15 min (with the temperature maintained at a maximum of 25° C.). The solution was stirred for 2–2.5 h at 15–25° C. Di-tert-butyl dicarbonate (BOC-anhydride) (54.56 g, 0.25 mol) was added and stirred for 10 min. Triethylamine (30.36 g, 0.30 mol) was then added to adjust the pH to between 8–9. The solution was stirred for 30 min and then cooled to 10–15° C. A solution of 25% aq. ammonium hydroxide (20.0 g, 0.29 mol) in water (480 g) was then added, while the temperature was maintained below 15° C. The solution was seeded and a solution of 25% aq. ammonium hydroxide (20.0 g, 0.29 mol) in water (480 g) was added. The resulting suspension was cooled to 0–5° C. and stirred for 2 h. The product was collected by filtration, washed with water (500 g) and dried in vacuo at 45° C.

Yield 343.34 g (96.9%), purity (LC) 99.6%.

EXAMPLE 9

(3aR,4R,6S,6aS)-(+)-Methyl 4-[[(1,1-dimethylethoxy)carbonyl]amino]-3-(1'-ethylpropyl)-3a,5,6,6a-tetrahydro-4H-cyclopent[d]isoxazole-6-carboxylate (3aR,4R,6S,6aS)-1,1-dimethylethylammonium 4-[[1,1-dimethylethoxy)carbonyl]amino]-3-(1'-ethylpropyl)-4,5,6,6a-tetrahydro-3aH-cyclopent[d]isoxazole-6-carboxylate (211 g, 0.51 mol) was suspended in acetone (400 g). Potassium carbonate (6.9 g, 0.05 mol) was added, followed by a solution of 30 wt % sodium hydroxide in water (66.7 g, 0.50 mol). 300 g of solvent were distilled off, acetone (300 g) was added, and then another 300 g of solvent were distilled off. The solution was cooled to 40–45° C. Dimethyl sulphate (91.0 g, 0.71 mol) was then added to the suspension. The resulting two phase system was stirred for 60 min at 40–45° C. and then cooled to 15–20° C. A solution of 25% aq. ammonium hydroxide (4.0 g, 0.06 mol) in water (96 g) was added. The reaction mixture was stirred for 20 min, methanol (100 g) was added, the reaction mixture was cooled to 0–5° C., seeded and stirred for 20 min, resulting in the crystallization of the product as fine needles. Over a period of 45 min a solution of 25% aq. ammonium hydroxide (6.0 g, 0.088 mol) in water (144 g) was added at 0–5° C. to complete crystallization. The product was collected by filtration, rinsed with water (300 g) and dried in vacuo at 45–50° C.

Yield 174.51 g (96.9%), purity (LC) 99.2%.

EXAMPLE 10

(1S,2S,3S,4R,1'S)-Methyl 3-[(1'-amino-2'-ethyl)butyl]-4-[[(1,1-dimethylethoxy)carbonyl]amino]-2-hydroxycyclopentane-1-carboxylate (3aR,4R,6S,6aS)-(+)-Methyl 4-[[(1,1-dimethylethoxy)carbonyl]amino]-3-(1'-ethylpropyl)-3a,5,6,6a-tetrahydro-4H-cyclopent[d]isoxazole-6-carboxylate (70.5 g, 0.20 mol) and nickel chloride hexahydrate (50.0 g, 0.21 mol) were dissolved in methanol (180 g). The green solution was cooled to 0–5° C. Sodium hydroxide (0.44 g, 0.01 mol) and sodium borohydride (20.0 g, 0.53 mol) were dissolved in methanol (160 g) and added over 2 h to the reaction mixture, while the reaction mixture temperature was maintained at 0–10° C. After complete addition of the borohydride solution, the reaction mixture was stirred for 30 min at 0–5° C. and then warmed to 10–15° C. 37 wt % hydrochloric acid (12.0 g, 0.122 mol) was added, followed by addition of a solution of sodium nitrite (7.0 g, 0.10 mol) in water (35 g), at a rate that maintained the reaction temperature at or below 25° C. After the addition of nitrite was complete, the pH of the solution was adjusted to 6.85 by adding 37 wt % hydrochloric acid (about 35.7 g, 0.36 mol). The reaction mixture was stirred at 20–25° C., until all of the black precipitate was dissolved and a green suspension was formed. A solution of ammonium chloride (22.0 g, 0.41 mol) in water (70 g) was added. 25% aq. ammonium hydroxide (about 180 g, 2.64 mol) was then added until a pH 9.6 was reached. A solution of 30 wt % of sodium hydroxide in water (about 20 g, 0.15 mol) was added to adjust the pH to 9.87. The mixture was stirred overnight at 20–25° C. The precipitate was collected by filtration and washed once with a solution of 25% aq. ammonium hydroxide (30 g) in water (170 g) to yield wet crude product (230 g).

The wet crude product was suspended in toluene (870 g). The suspension was heated to 75–80° C. for 20 min. A two-phase system was obtained. The phases were separated, and 25% aq. ammonium hydroxide (110 g) was added to the organic phase. The mixture was again heated to 80° C., the phases were separated, and 25% aq. ammonium hydroxide (110 g) was again added to the organic phase. The mixture was again heated to 80° C., the phases were separated and the organic layer was cooled to 0–5° C. over 1.5 h. The product was collected by filtration and rinsed with toluene (30 g). The wet product was dried in vacuo at 40–50° C.

Yield 51.63 g (70%), purity (LC) 96.7%.

EXAMPLE 11

(1S,2S,3R,4R,1'S)-(−)-3-[(1'-Acetylamino-2'-ethyl)butyl]-4-[[(aminoimino)methyl]amino]-2-hydroxycyclopentan-1-carboxylic Acid (1S,2S,3S,4R,1'S)-Methyl 3-[(1'-amino-2'-ethyl)butyl]-4-[[(1,1-dimethylethoxy)carbonyl]amino]-2-hydroxycyclopentane-1-carboxylate (2990 g, 8.34 mol) was suspended in toluene (17090 g) and heated to 48–53° C. Acetic anhydride (929 g, 9.10 mol) was added to the slurry over 40 min at 48–53° C. After the addition of the acetylating agent was finished the resulting solution was then stirred for about 3 min, then as quickly as possible, a solution of 25% aq. ammonium hydroxide (752 g, 11.0 mol) in water (3002 g) was added. The phases were separated, the aqueous phase was discarded, while the organic phase was washed once with water (3751 g). The organic phase was then added to 37 wt % hydrochloric acid (3277 g, 33.3 mol) over 30 min, at 0–10° C. After stirring for 2 h at 8–12° C., the layers were separated, and the organic layer was washed with water (1439 g). The combined aqueous layers were treated with a 30 wt % solution of sodium hydroxide (a total of 4807.5 g, 36.06 mol) in water—the first portion (about 2750 g, 20.57 mol) was added at 0–10° C., resulting in a rise in pH to about neutral pH, the second portion (exactly 1.85 equivalents, 2057.5 g, 15.43 mol) was then added at −5–5° C. over a period of 2 h. The solution was stirred for an additional 60 min at about 0° C. 1,2,4-Triazole-1-formamidine hydrochloride (1501 g, 10.2 mol) was then added at 0–5° C. The suspension was stirred for 15 min, the temperature was allowed to come to 20–25° C., and the pH was adjusted to 8.3–8.5 by adding 30% aq. sodium hydroxide solution (227 g, 1.70 mol). A clear solution was formed. After about 2 h a white solid started to precipitate. The reaction mixture was stirred at room temperature overnight while the pH decreased to 8.5. The suspension was cooled to 0–5° C. and stirred for additional 2–3 h. The product was collected by filtration, and washed with water (1160 g).

EXAMPLE 12

Recrystallization of (1S,2S,3R,4R,1'S)-(−)-3-[(1'-Acetylamino-2'-ethyl)butyl]-4-[[(aminoimino)methyl]amino]-2-hydroxycyclopentan-1-carboxylic Acid Crude (1S,2S,3R,4R,1'S)-(−)-3-[(1'-Acetylamino-2'-ethyl)butyl]-4-[[(aminoimino)methyl]amino]-2-hydroxycyclopentan-1-carboxylic acid (3142 g) was suspended in water (10656 g). The suspension was heated to reflux and 655 g of solvent were distilled off. The suspension was cooled to at 70–80° C. and water (655 g) was added. Activated carbon (Norit® C, 33 g) and methanol (2110 g) were added. The reaction mixture was heated to reflux and filtered over Hyflo Super Cel® (100 g) The filter cake was washed with methanol (100 g) The combined filtrates were again heated to reflux, and solvent was distilled off until a boiling point of 99–100° C. was reached. The mixture was cooled to 70–80° C., during which time the product precipitated. The mixture was stirred overnight at 70–80° C., until phase transformation to form A had taken place. The suspension was then cooled to 0–5° C. The solid was collected by filtration, rinsed with cold (0–10° C.) water (1302 g) and air dried over a bowl of water to yield Form A product as a trihydrate, as white solid/crystals.

Yield: 2297 g, purity 99.91%; mp 256–258° C. (decomposition).

We claim:
1. A process for preparing a compound of the formula (Ib):

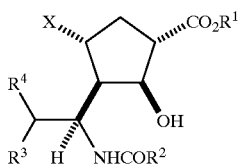

(Ib)

wherein
$R^1$ is selected from the group consisting of hydrogen, alkyl, cycloalkyl, aryl and aralkyl;
$R^2$ is selected from the group consisting of hydrogen; alkyl, cycloalkyl, halogen substituted alkyl, aryl and substituted aryl;
$R^3$ and $R^4$ are independently selected from the group consisting of hydrogen, alkyl, alkylene, cycloalkyl, aryl and substituted aryl, provided that at least one of $R^3$ or $R^4$ is alkyl;
X is $NHC(=NH)NH_2$;
and pharmaceutically acceptable salts thereof;
comprising
reacting an N-protected compound of formula (II), wherein W is an N-protecting group,

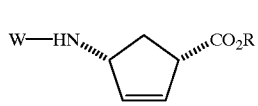

(II)

with a nitride oxide of formula (III),

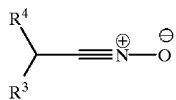

(III)

at a temperature which prevents uncontrolled decomposition of the compound of formula (III), to yield the compounds of formula (IV) and (IV');

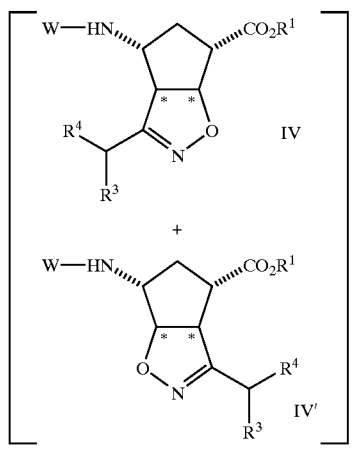

reacting the mixture of the compounds of formula (IV) and (IV') with alkali or tetra alkyl ammonium hydroxides to form the corresponding alkali metal salts of formula (V) and (V'), where
$M^+$ represents an alkali metal cation or a tetra-alkylammonium cation;

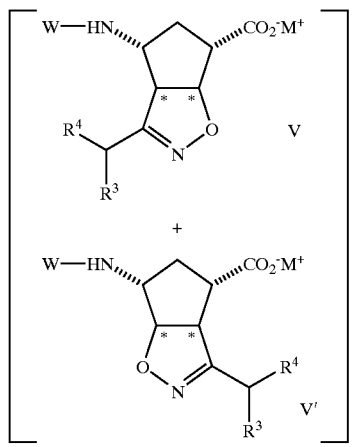

reacting the mixture of the compounds of formula (V) and (V') with an acid to form the corresponding acids of formula (VI) and (VI');

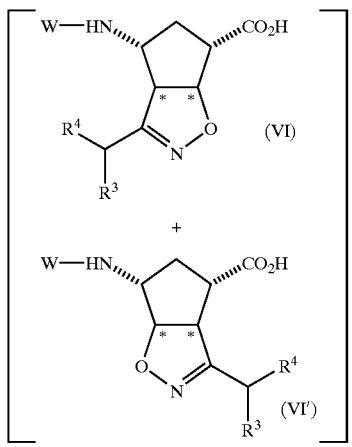

reacting the compounds of formula (VI) and (VI') with ammonia or an amine to precipitate the corresponding salt of formula (VII), where Q' represents $NH_4^+$ or substituted ammonium cation;

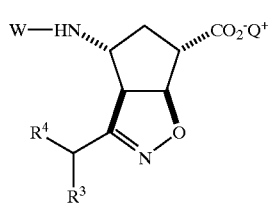

reacting the compound of formula (VII) with $R^1OH$ and treating with a nonaqueous acid, to yield the compound of formula (IVa), and when the N-protecting group on compound (VII) is t-butoxycarbonyl (Boc), the solution is further treated with di-tert-butyl dicarbonate and a tertiary amine;

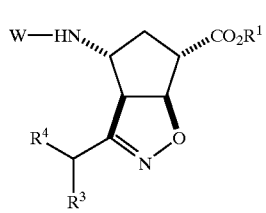

reducing the compound of formula (IVa) using sodium borohydride and $NiCl_2$ to yield the corresponding aminoalcohol of formula (IX);

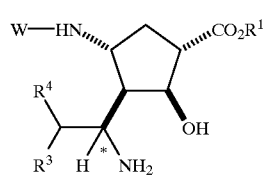

recrystallizing the compound of formula (IX) from an organic solvent or an alcohol/water mixture, to isolate the corresponding compound of formula (IXa);

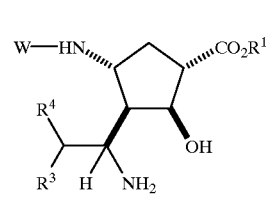

reacting the compound of formula (IXa) with a compound of formula (X), $(R^2CO)_2O$, or a compound of formula (XI), $R^2COV$, where $R^2$ is as described above and V is chlorine or bromine, to produce the corresponding compound of formula (XII);

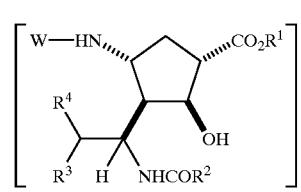

removing the N-protecting group from the compound of formula (XII) to produce the corresponding compound of formula (XIII), or salt thereof,

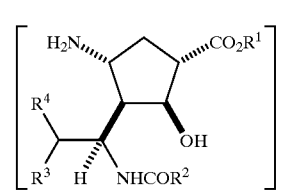

reacting compound of formula (XIII) with a base to produce the corresponding acid salt of formula (XIV);

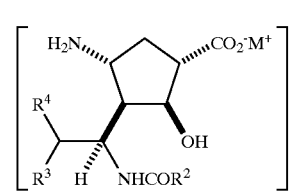

reacting the compound of formula (XIII) with guanylating agent, to produce compound (Ib) when $R^1$=alkyl, cycloalkyl and aralkyl and reacting the compound (XIV) with a guanylating agent, to produce the corresponding compound of formula (Ib), when $R^1$=H.

2. A process for preparing a compound of formula (I):

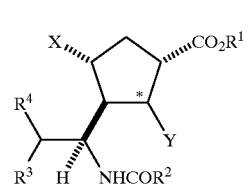

wherein

R¹ is selected from the group consisting of hydrogen, alkyl, cycloalkyl, aryl and aralkyl;

R² is selected from the group consisting of hydrogen; alkyl, cycloalkyl, halogen substituted alkyl, aryl and substituted aryl;

R³ and R⁴ are independently selected from the group consisting of hydrogen, alkyl, alkylene, cycloalkyl, aryl and substituted aryl, provided that at least one of R³ or R⁴ is alkyl;

X is $NHC(=NH)NH_2$;

Y is selected from the group consisting of hydrogen, fluorine, hydroxy, $OR^5$, $OCOR^5$, $NH_2$, $NHCOR^5$ and $NR^5R^6$, where $R^5$ is selected from alkyl, aryl, $COR^6$ or $COOR^6$; and where $R^6$ is selected from hydrogen, alkyl, alkylene, cycloalkyl, aryl or substituted aryl;

and pharmaceutically acceptable salts thereof;

comprising
  reacting an N-protected compound of formula (II), wherein W is an N-protecting group,

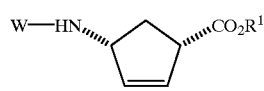

(II)

with a nitrile oxide of formula (III),

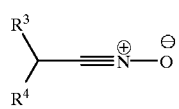

(III)

at a temperature which prevents uncontrolled decomposition of the compound of formula (III), to yield the compounds of formula (IV) and (IV');

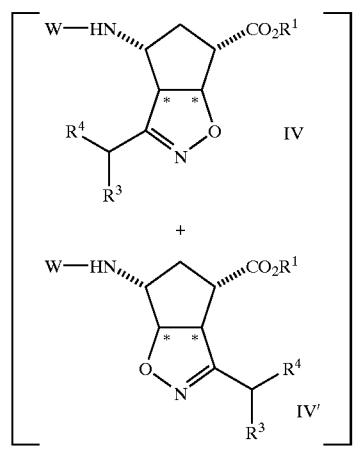

reacting the mixture of the compounds of formula (IV) and (IV') with alkali or tetra alkyl ammonium hydroxide to the corresponding alkali metal salts of formula (V) and (V'), where M⁺ represents an alkali metal cation or a tetra-alkyl-ammonium cation;

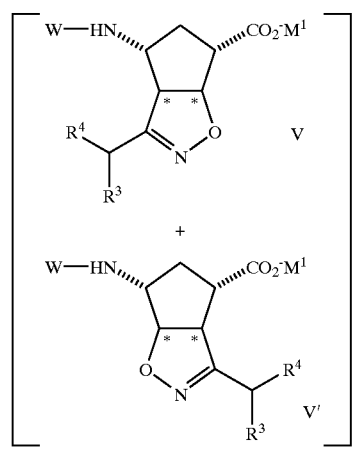

reacting the mixture of the compounds of formula (V) and (V') with an acid to form the corresponding acids of formula (VI) and (VI');

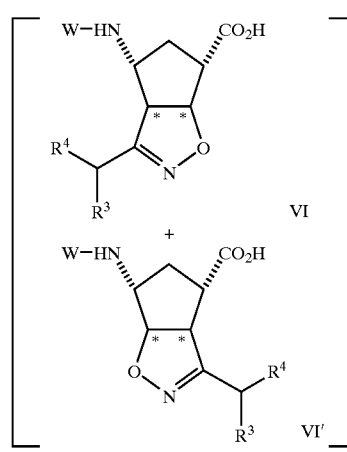

reacting the compounds of formula (VI) and (VI') with ammonia or an amine to precipitate the corresponding salt of formula (VII), where Q' represents $NH_4^+$ or substituted ammonium cation;

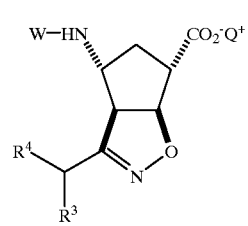

(VII)

reacting the compound of formula (VII) with R¹OH and treating with a nonaqueous acid, to yield the compound of formula (IVa), when the N-protecting group on compound (VII) is t-butoxycarbonyl (Boc), the solution is further treated with di-tert-butyl dicarbonate and tertiary amine;

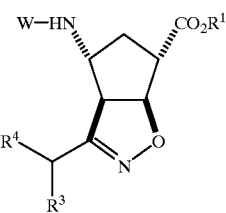

(IVa)

reducing the compound of formula (IVa) using sodium borohydride and NiCl$_2$ to yield the corresponding aminoalcohol of formula (IX);

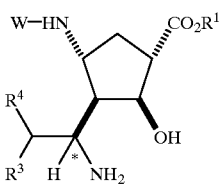

(IX)

recrystallizing the compound of formula (IX) from an organic solvent or an alcohol/water mixture, to isolate the corresponding compound of formula (IXa);

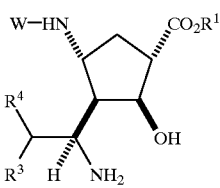

(IXa)

reacting the compound of formula (IXa) with a compound of formula (X), (R$^2$CO)$_2$O, or a compound of formula (XI), R$^2$COV, where R$^2$ is as described above and V is chlorine or bromine, to produce the corresponding compound of formula (XII);

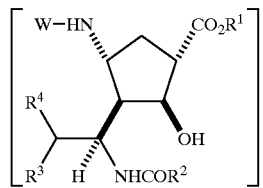

XII converting the compound of formula (XII) to the compound of formula (XII');

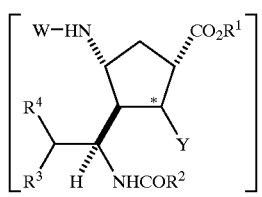

XII' removing the N-protecting group from the compound of formula (XII') with a base to produce the corresponding compound of formula (XIII'), or salt thereof;

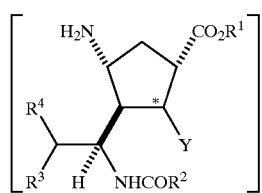

XIII' reacting the compound of formula (XIII') to the corresponding acid salt of formula (XIV');

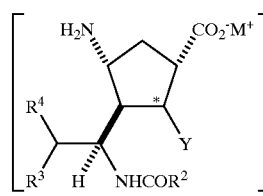

XIV' reacting the compound of formula (XIII') with guanylating agent, to produce compound (I) when R$^1$=alkyl, cycloalkyl and aralkyl and reacting the compound (XIV') with a guanylating agent, to produce the corresponding compound of formula (I), when R$^1$=H.

3. A process for preparing a compound of the formula (Ib):

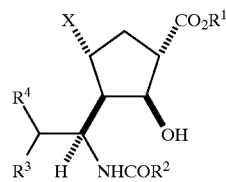

(Ib)

wherein

R$^1$ hydrogen;

R$^2$ is selected from the group consisting of hydrogen; alkyl, cycloalkyl, halogen substituted alkyl, aryl and substituted aryl;

R$^3$ and R$^4$ are independently selected from the group consisting of hydrogen, alkyl, alkylene, cycloalkyl, aryl and substituted aryl, provided that at least one of R$^3$ or R$^4$ is alkyl;

X is NHC(=NH)NH$_2$;

and pharmaceutically acceptable salts thereof;

comprising reacting an N-protected compound of formula (II), wherein W is an N-protecting group,

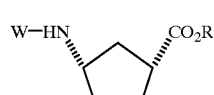

(II)

with a nitrile oxide of formula (III),

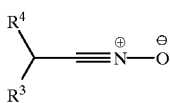
(III)

at a temperature which prevents uncontrolled decomposition of the compound of formula (III), to yield the compounds of formula (VI) and (VI');

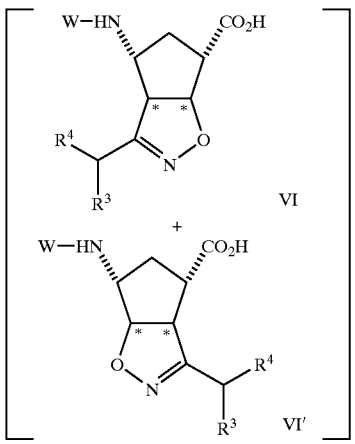

reacting the mixture of the compounds of formula (VI) and (VI') with ammonia or an amine to precipitate the corresponding salt of formula (VII), where $Q^+$ represents $NH_4^+$ or substituted ammonium cation;

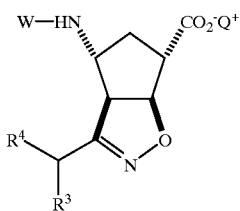
(VII)

reacting the compound of formula (VII) with $R^1OH$, preferably ortho ester and treating with a nonaqueous acid, such as HCl gas or HBr gas to yield the compound of formula (IVa), if N-protecting group on compound (VII) is t-butoxycarbonyl (Boc), the solution is further treated with di-tert-butyl dicarbonate and a tertiary amine;

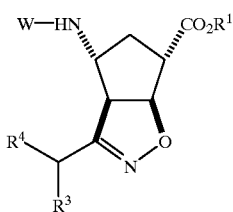
(IVa)

reducing the compound of formula (IVa) using sodium borohydride and $NiCl_2$ to yield the corresponding aminoalcohol of formula (IX);

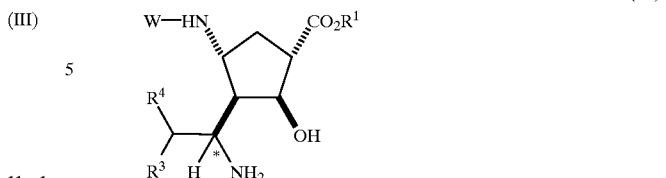
(IX)

recrystallizing the compound of formula (IX) from an organic solvent or an alcohol/water mixture, to isolate the corresponding compound of formula (IXa);

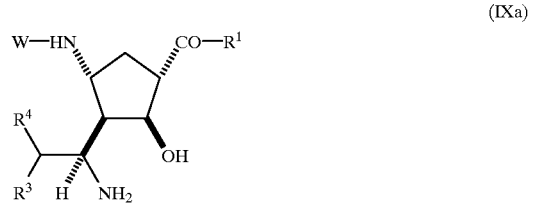
(IXa)

reacting the compound of formula (IXa) with a compound of formula (X), $(R^2CO)_2O$, or a compound of formula (XI), $R^2COV$, where $R^2$ is as described above and V is chlorine or bromine, to produce the corresponding compound of formula (XII);

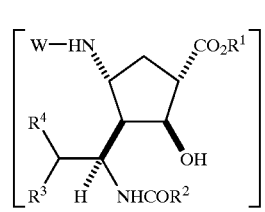
XII removing the N-protecting group from the compound of formula (XII) to produce the corresponding compound of formula (XIII), or salt thereof;

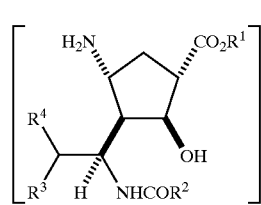
XIII reacting the compound of formula (XIII) with a base to produce the corresponding acid salt of formula (XIV);

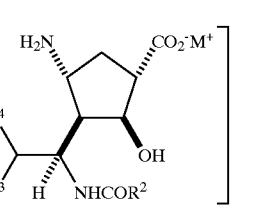
XIV reacting the compound (XIV) with a guanylating agent, to produce the corresponding compound of formula (Ib), wherein $R^1$=H.

4. The process of claim 1, wherein the compound of formula (Ib) is represented by the formula (Ia):

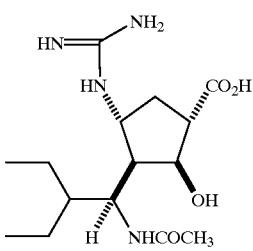

(Ia)

5. The process of claim 4, wherein the N-protecting group is t-butxoycarbonyl.

6. The process of claim 5, further comprising adding the compound of formula (II) to the compound of formula (III) at a temperature of 40–90° C., in the presence of a tertiary amine.

7. The process of claim 6, wherein, when the compounds of formula (VI) and (VI') are reacted with an amine, the amine is t-butylamine.

8. The process of claim 7, further comprising treating the compound of formula (IVa) with di-tert-butyl dicarbonate and triethylamine.

9. The process of claim 8, further comprising reducing the compound of formula (IVa) with about 2–3 molar equivalents of sodium borohydride and at least 1 molar equivalents of $NiCl_2$.

10. The process of claim 9, further comprising isolating the compound of formula (IX) by adding sodium nitrite.

11. The process of claim 10, wherein in recrystallizing the compound of formula (IXa), the organic solvent is toluene.

12. The process of claim 11, wherein the compound of formula (IXa) is reacted with about 1 equivalent of the compound of formula (X), in toluene.

13. The process of claim 12, wherein the N-protecting group on the compound of formula (XII) is removed with aqueous hydrochloric acid.

14. The process of claim 13, wherein the guanylating agent is 1H-pyrazole-1-carboxamidine, monohydrochloride.

15. The process of claim 13, wherein the guanylating agent is 1H-triazole-1-carboimidamide, monohydrochloride.

16. The process of claim 15, further comprising reacting the compound of formula (XIV) with the guanylating agent at a pH about 8.5 and a temperature in the range of 20–30° C.

17. The process of claim 1 wherein the reacting the compound of formula (VII) with $R^1OH$ further comprises treating with an ortho ester and wherein said nonaqueous acid comprises HCl gas or HBr gas.

18. The process of claim 2 wherein the reacting the compound of formula (VII) with $R^1OH$ further comprises treating with an ortho ester and wherein said nonaqueous acid comprises HCl gas or HBr gas.

19. The process of claim 3 wherein the reacting the compound of formula (VII) with $R^1OH$ further comprises treating with an ortho ester and wherein said nonaqueous acid comprises HCl gas or HBr gas.

* * * * *